(12) United States Patent
Kim

(10) Patent No.: US 9,140,804 B2
(45) Date of Patent: Sep. 22, 2015

(54) METHODS AND SYSTEMS FOR DETERMINING TIMING RECOVERY INFORMATION IN A POSITRON EMISSION TOMOGRAPHY (PET) SYSTEM

(75) Inventor: Chang Lyong Kim, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 335 days.

(21) Appl. No.: 13/436,032

(22) Filed: Mar. 30, 2012

(65) Prior Publication Data

US 2013/0256536 A1 Oct. 3, 2013

(51) Int. Cl.
*G01T 1/164* (2006.01)
*G01T 1/29* (2006.01)
*G01T 1/202* (2006.01)
*G01T 1/20* (2006.01)

(52) U.S. Cl.
CPC ............. *G01T 1/1648* (2013.01); *G01T 1/2985* (2013.01); *G01T 1/20* (2013.01); *G01T 1/202* (2013.01)

(58) Field of Classification Search
CPC ......... G01T 1/20; G01T 1/202; G01T 1/2985; G01T 1/1648; G01T 1/1644; G01T 1/172; A61B 6/037
USPC ................................ 250/352, 363.02, 370.11
See application file for complete search history.

(56) References Cited

U.S. PATENT DOCUMENTS

| | | | | |
|---|---|---|---|---|
| 7,820,977 | B2* | 10/2010 | Beer et al. | 250/390.07 |
| 2010/0219345 | A1* | 9/2010 | Franch et al. | 250/362 |
| 2011/0210255 | A1 | 9/2011 | Kim | |
| 2013/0032706 | A1* | 2/2013 | Cho | 250/252.1 |
| 2013/0214168 | A1* | 8/2013 | McDaniel et al. | 250/362 |

OTHER PUBLICATIONS

Consentino, et al, "High-resolution Time-Of-Flight PET with Depth-Of-Interaction becomes feasible: a proof of principle," (undated).
S. Seifert, et al., "Ultra precise timing with SiPM-based TOF PET scintillation detectors", IEEE NSS-MIC Sym. Conf. record, pp. 2329-2333, USA 2009.
C. Degenhardt et al., "The Digital Silicon Photomultiplier—A Novel Sensor for the Detection of Scintillation Light", IEEE NSS-MIC Sym. Conf. record, pp. 2383-2386, USA 2009.
C. L. Kim, G-C. Wang, S. Dolinsky, "Multi-Pixel Photon Counters for TOF PET Detector and its Challenges", IEEE Trans. Nucl. Sci., vol. 56, No. 5, pp. 2580-2585, Oct. 2009.
C. L. Kim, et al., "Dependence of Timing Resolution on Crystal Size for TOF PET", IEEE NSS-MIC Symposium Conference record, 2007, Hawaii USA.

* cited by examiner

*Primary Examiner* — Yara B Green
(74) *Attorney, Agent, or Firm* — Dean D. Small; The Small Patent Law Group, LLC.

(57) ABSTRACT

A method and system for determining timing recovery information in a positron emission tomography (PET) system. One method includes determining energy information from pairs of light sensors of detectors of the TOF PET system, determining timing information from the pairs of light sensors of the detectors of the TOF PET system and calculating timing recovery information using the determined energy and timing information.

22 Claims, 6 Drawing Sheets

METHODS AND SYSTEMS FOR DETERMINING TIMING RECOVERY INFORMATION IN A POSITRON EMISSION TOMOGRAPHY (PET) SYSTEM

BACKGROUND OF THE INVENTION

This subject matter disclosed herein relates generally to medical imaging systems, and more particularly, to Positron Emission Tomography (PET) systems, such as Time of Flight (TOF) PET systems.

A PET system generates images that represent the distribution of positron-emitting nuclides within the body of a patient. When a positron interacts with an electron by annihilation, the entire mass of the positron-electron pair is converted into two 511 keV photons. The photons are emitted in opposite directions along a line of response. The annihilation photons are detected by detectors that are placed along the line of response on a detector ring. When these photons arrive and are detected at the detector elements at the same time, this is referred to as coincidence. An image is then generated based on the acquired image data that includes the annihilation photon detection information.

In PET systems, the image quality depends on image statistics. The image statistics may be improved by acquiring the image data for longer durations. However, the total time required to acquire the image data is limited by the lifetime of the radioactive isotope used in the imaging process and by the inability of the patients to remain immobile for extended durations. Image quality may be improved by including TOF information of the emission data, which generally refers to the difference in the time at which the photons are detected by the detector elements. The timing difference is used to localize the source of emission along the line joining two detector elements in TOF PET systems.

In order to maintain a good signal-to-noise ratio in the images in the reconstruction process in TOF PET systems, these systems need to accurately calculate the timing difference. The timing capability of PET systems depends on different factors including the amount of "fast" light output from the scintillator and the quantum efficiency of photosensors of detectors of these systems, as well as geometrical factors, such as the transmission efficiency in scintillators of the detectors, light collection methods and efficiency, the size of the detectors, the reflective material used, and the refractive index of matching of the material used, among others.

With respect to the timing resolution of PET systems, the crystal size of the detectors affects the timing resolution due to the spread of gamma ray interaction points and the degree of scintillation light spread/loss inside a crystal. Smaller and more flat crystals are less sensitive to both types of spreads and can provide improved timing resolution. However, smaller crystals may not have enough stopping power to be used in particular detectors, such as whole body PET detectors.

BRIEF DESCRIPTION OF THE INVENTION

In one embodiment, a method for determining timing recovery information in a Time-of-Flight (TOF) Positron Emission Tomography (PET) system is provided. The method includes determining energy information from pairs of light sensors of detectors of the TOF PET system, determining timing information from the pairs of light sensors of the detectors of the TOF PET system and calculating timing recovery information using the determined energy and timing information.

In another embodiment, a Time-of-Flight (TOF) Positron Emission Tomography (PET) system is provided. The TOF PET system includes a plurality of detector elements configured to acquire scan data, wherein the detector elements have scintillator crystals with pairs of light sensors. The TOF PET system also includes a processor configured to calculate timing recovery information by determining energy information from the pairs of light sensors of detectors and determining timing information from the pairs of light sensors.

DETAILED DESCRIPTION OF THE INVENTION

Figure 1:
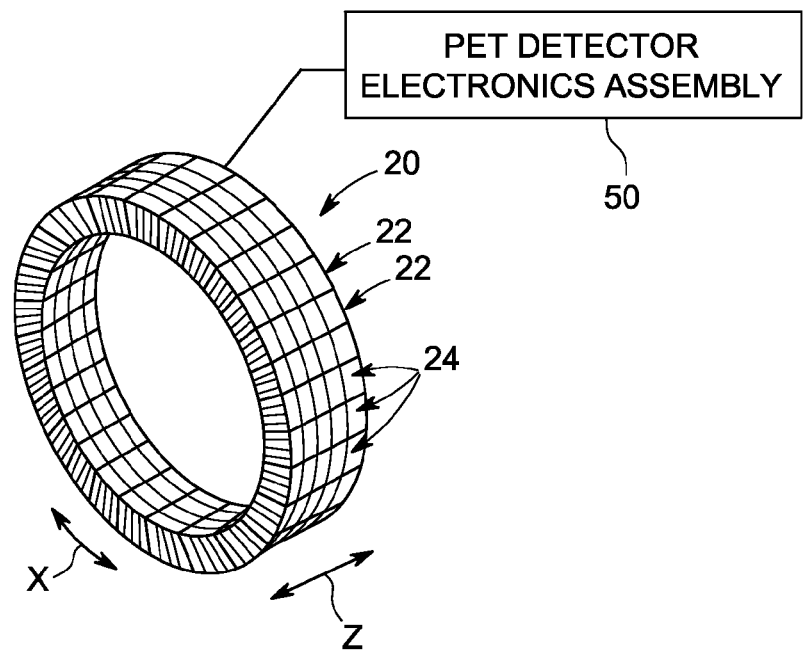
FIG. 1 is a perspective view of a positron emission tomography (PET) detector assembly in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for determining timing recovery information in Positron Emission Tomography (PET) systems, such as Time of Flight (TOF) PET systems. Thus, particular embodiments provide for timing recovery methods for TOF PET systems. At least one technical effect of various embodiments is to provide the timing resolution of detectors having smaller crystals while using larger crystals in the PET detectors.

Various embodiments may be used in a PET system having a PET detector assembly 20 shown in perspective view in FIG. 1. The PET detector assembly 20 is coupled to a PET detector electronics assembly 50 that includes electronics for processing received PET data and recovering timing data or information as described in more detail herein. For example, the PET detector electronics assembly 50 may receive one or more signals from a plurality of application specific integrated circuits (ASICs) connected to the PET detector assembly 20. Thus, the PET detector ring assembly 20 may be utilized to provide signals to the PET detector electronics assembly 50.

In various embodiments, the PET detector assembly 20 includes a plurality of detector modules 22 that are arranged in a ring to form the PET detector ring assembly 20. Each detector module 22 is assembled from a plurality of detector units 24. Thus, a plurality of detector units 24 is assembled to form a single detector module 22, and a plurality of detector modules 22 is assembled to form the detector ring assembly 20. In one embodiment, the detector assembly 20 includes twenty-eight detector modules 22 that are coupled together such that the detector assembly 20 has a ring shape. In some embodiments, each detector module 22 includes twenty detector units 24 that are arranged in a 4×5 matrix. It should be realized that the quantity of detector modules 22 utilized to form the detector assembly 20 is exemplary, and that the detector assembly 20 may have more than or fewer than twenty-eight detector modules 22. Moreover, it should be realized that quantity of detector units 24 utilized to form each detector module 22 is exemplary, and that the detector module 22 may have more than or fewer than twenty detector units 24.

Figure 2:
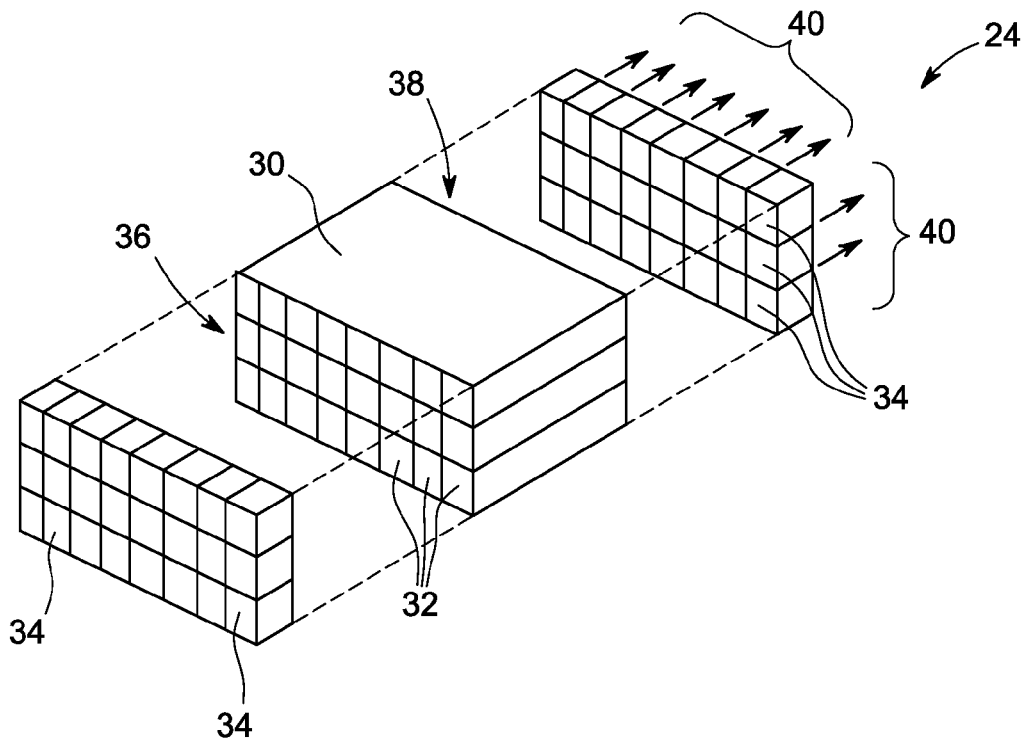
FIG. 2 is a perspective view of a detector unit formed in accordance with an embodiment.

FIG. 2 is a perspective view of an exemplary detector unit 24 that may form a portion of the detector module 22 shown in FIG. 1. In various embodiments, the detector unit 24 includes a scintillator block 30 having one or more scintillator crystals 32 that are arranged along an x-axis and a z-axis. In one embodiment, the scintillator block 30 has thirty-six crystals 32 that are arranged in a 4×9 matrix. However, it should be realized that the scintillator block 30 may have fewer than or more than thirty-six crystals 32, and that the crystals 32 may be arranged in a matrix of any suitable size. It also should be noted that the scintillator crystals 32 may be formed from any suitable material such as bismuth germinate (BGO), Cerium-doped Lutetium Yttrium Orthosilicate (LYSO) or Gadolinium Oxyorthosilicate (GSO), among others.

The detector unit 24 also includes a plurality of light sensors 34, illustrated as a plurality of photosensors, which may be any suitable photo-detectors that sense or detect light or other electromagnetic energy. In the illustrated embodiment, a plurality of light sensors 34 are coupled to both ends 36 and 38 of the scintillator block 30 (illustrated as opposite ends) to form a Depth-of-Interaction (DOI) detector. Thus, various embodiments do not include any reflector or reflective material on one of the ends of the scintillator block 30.

In various embodiments, the detector unit 24 has eighteen light sensors 34 on each end of the scintillator block 30 that are arranged in a 3×6 matrix. However, it should be realized that the detector unit 24 may have fewer than or more than eighteen light sensors 34 and that the light sensors 34 may be arranged in a matrix of any suitable size. For example, some embodiments include 36, 54 or 100 crystals 32 having corresponding light sensors 34 that are arranged in a 6×6 matrix, 9×6 matrix or 10×10 matrix, respectively. Thus, various embodiments may provide a one-to-one coupling between the light sensor 34 (e.g., a photosensor) and the crystal 32, or there may be a one-to-multiple coupling between the light sensor 34 and the crystal 32.

In one embodiment, the light sensors 34 are avalanche photodiodes that are connected in parallel and operated above a breakdown voltage in a Geiger mode. For example, the light sensors 34 may be silicon photomultipliers (SiPMs) in various embodiments that are configured as single photon sensitive devices formed from an avalanche photodiode array on a silicon substrate. However, it should be noted that the light sensors 34 may be any type of light sensor, for example, any type of photosensor. In some embodiments, for example, the light sensor 34 may be any type of light sensor that may be used for fast timing measurements.

In operation, the scintillator crystals 32 convert the energy, deposited by a gamma ray impinging on the scintillator crystal 32, into visible (or near-UV) light photons. The photons are then converted to electrical analog signals by the light sensors 34. More specifically, when a gamma ray impinges on any one of the scintillators 32 in a detector unit 24, the scintillator detecting the gamma ray converts the energy of the gamma ray into visible light that is detected by the light sensors 34 in the detector unit 24. Thus, in the exemplary embodiment, each detector unit 24 is configured to output n analog signals 40, wherein in various embodiments, n=36×2=52, such that a pair of analog signals 40 represents the information output from a respective pair of light sensors 34.

Figure 3:
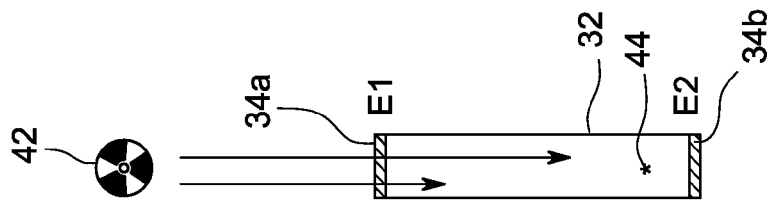

Using the measured energy (detected from an emission source 42, such as a radionuclide injected into a patient) from each pair of light sensors 34 (namely from both ends of the scintillator block 30), the gamma ray interaction depth can be calculated as illustrated in FIG. 3. Additionally, timing recovery information may be determined as described below.

In particular, the ratio of E1 and E2 (the energy detected at each of the light sensors 34) is used to calculate the interaction points within the scintillator crystal 32 to determine DOI information. The DOI information may also be calculated using any suitable method and is determined based on the travel time difference between the interaction time for the pair of light sensors 34 (shown as top and bottom light sensors 34). However, DOI information also may be calculated or provided using the ratio of E1 and E2. Also, T1-T2 may be used. For example, scintillation light (i.e., a visible photon) is generated within the crystal 32 by the interaction of a gamma photon with the crystal 32. Using the ratio of the energy measured at each of the light sensors 34a and 34b, the interaction point 44 within the crystal 32 is determined. It should be noted that the detected energy by the light sensors 34 is greater the closer the interaction is to the light sensor 34. Also, the difference between T1 and T2 may be used to calculate the DOI information, for example, when timing approaches the 30 pico-second (p)s range.

Figure 4:
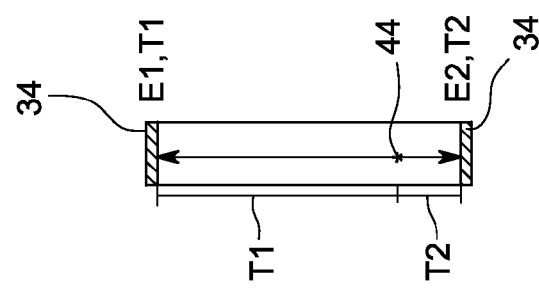
FIGS. 3 and 4 are diagrams of a crystal of the detector unit of FIG. 2 illustrating light sensors in accordance with an embodiment.

Additionally, timing recovery information also may be determined such that a DOI TOF detector arrangement is provided. For example, using the time that each of the light sensors 34 detected the interaction (illustrated as T1 and T2), such as based on a recorded time stamp, a determination may be made to correct for the scintillation photon transit time (or distance) difference along the crystal. This removes the transit time difference depending on the interaction point along the crystal. It should be noted that this determination may be performed before weighting (as described in more detail herein) in various embodiments. Thus, in various embodiments, the DOI structure of various embodiments provide for recovering timing resolution using both energy information (E1,E2) and timing information (T1,T2) as illustrated in FIG. 4. In particular, the ratio of E1 and E2 provides DOI information that can be used to correct for the scintillation photon transit time (or distance) difference. Additionally, as described in more detail herein, the T1 and T2 timing can be used to obtain a weighted timing.

In various embodiments, the DOI for a crystal of the detector is determined from the timing information from the pairs of light sensors of the detectors. Additionally, a time stamp, as described in more detail herein, may be corrected by an amount of a transit time calculated from a DOI point in the crystal.

Figure 5:
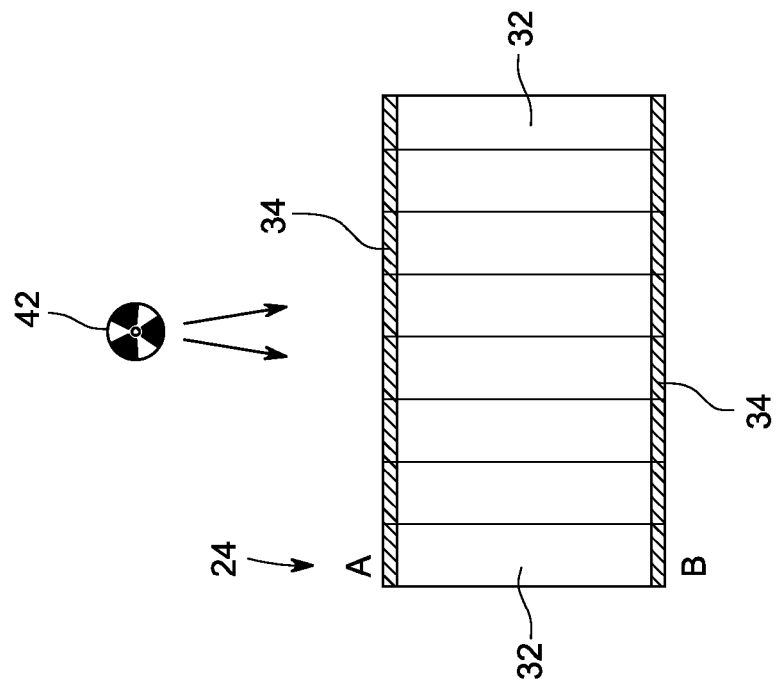
FIG. 5 is a diagram illustrating crystals of a detector unit having a radial placement of crystals and showing light sensors in accordance with an embodiment.
Figure 6:
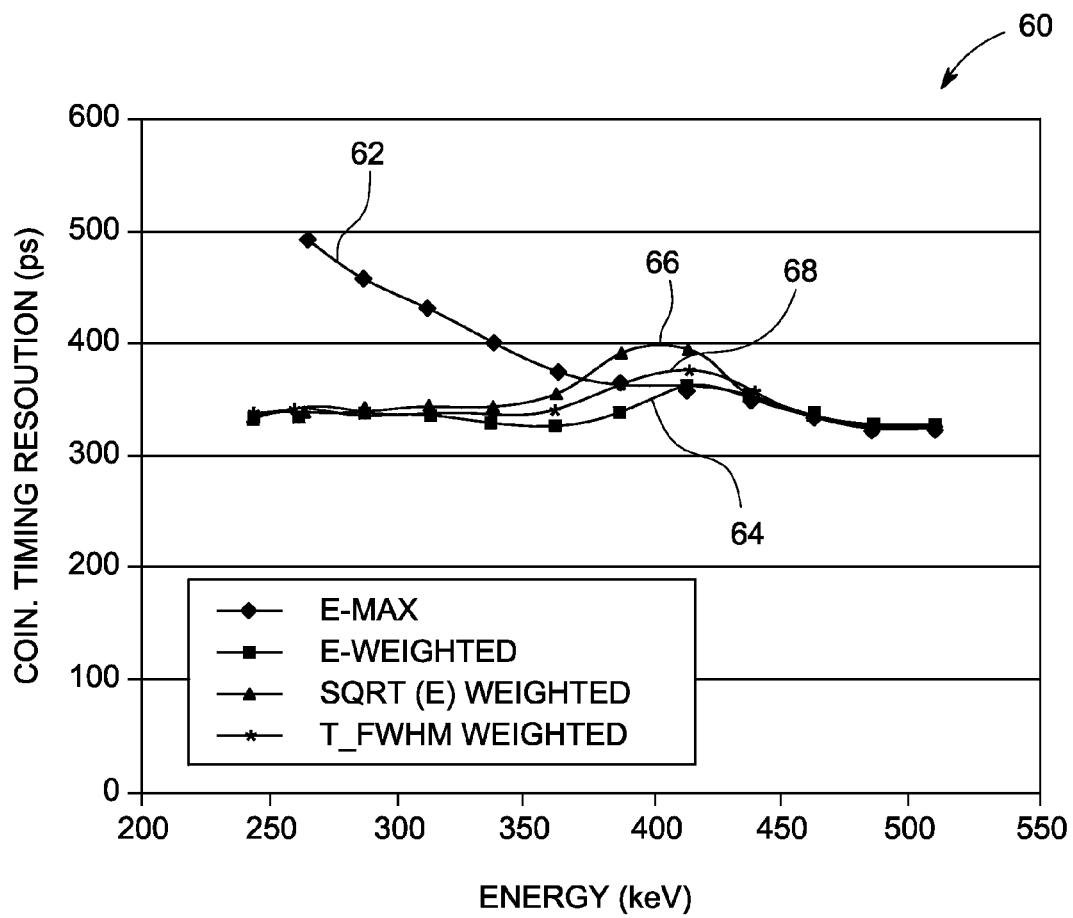
FIG. 6 is a graph illustrating exemplary coincidence timing resolution in accordance with various embodiments.

The various embodiments may include, for example, a plurality of light sensors 34 along the ends 36 and 38 of corresponding crystals 32 as shown in FIG. 5. For example, each of the crystals 32 includes a light sensor 34 at each end thereof. It should be noted that the crystals 32 may have different lengths. For example, in one embodiment, the crystals 32 have a length of about 25 mm. FIG. 6 illustrates a graph 60 showing coincidence timing resolution for Compton scattered events when a 511 KeV gamma ray deposits energy in a 25 mm long crystal 32, such that each light sensor receives a fraction of the gamma ray energy that sums to 511 KeV. In the graph 60, the horizontal axis represents Energy (in KeV) and the vertical axis represents Coincidence Timing Resolution (in pico-seconds).

In the graph 60, the curve 62 corresponds to the coincidence timing resolution in the case where the timing resolution is from the light sensor 34 having more energy recorded thereon. For example, if E1 is greater than E2, the timing from the E1 light sensor 34 is used. Thus, the curve 62 represents an E-max plot. The curve 64 represents an E weighted curve. In particular, the E weighted curve provides an energy weighted timing determined as follows: (T1*E1+T2*E2)/(E1+E2). The curve 66 represents a square root of E (sqrt(E)) curve. The sqrt(E) curve 66 in various embodiments provides timing information determined as follows: (T1*sqrt(E1)+T2*sqrt(E2))/(sqrt(E1)+sqrt(E2)). The curve 68 represents a full width at half maximum (FWHM) weighted curve. The T-FWHM curve 68 in various embodiments provides timing information determined as follows: 1/T-FWHM. Thus, timing recovery information may be determined in various embodiments using any of the equations above.

However, it should be noted that the timing recovery information may be calculated in different ways using E1 and E2 and/or T1 and T2. Thus, in various embodiments, the acquired information may be used in other methods to calculate the timing recovery information. For example, different weighting schemes may be used as desired or needed to calculate the timing recovery information.

It also should be noted that energy and timing information may be used from a plurality of crystals 32. Thus, various embodiments may use the determined or measured E and/or the determined or measured T from two of more crystals 32, which is indicated as Ei and/or Ti, where i corresponds to the number of crystals 32, which may be 1 or more. Accordingly, in various embodiments, i is an integer value greater than zero.

Various embodiments determine timing recovery information for Compton scatter events for or that involve two or more crystals 32 for one gamma ray event. Accordingly, various embodiments include the next crystal 32 or channel timing information. For example, four crystals 32 may be used, such that the timing recovery information comprises may be calculated as an energy weighted timing using:

(T1*E1+T2*E2+T3*E3+T4*E4)/(E1+E2+E3+E4)

where T1, T2, T3 and T4 is the determined timing information from a plurality of light sensors 34 and E1, E2, E3 and E4 is the determined energy information from the plurality of light sensors 34.

As another example, the timing recovery information may include calculating a square-root energy sqrt(E) weighted timing using:

(T1*sqrt(E1)+T2*sqrt(E2)+T3*sqrt(E3)+T4*sqrt(E4))/(sqrt(E1)+sqrt(E2)+sqrt(E1)+sqrt(E2))

where T1, T2, T3 and T4 is the determined timing information from a plurality of light sensors 34 and E1, E2, E3 and E4 is the determined energy information from the plurality of light sensors 34.

Thus, the various embodiments may be extended to use information from light sensors 34 for any number of crystals 32. For example, the timing recovery information may be calculated as an energy weighted timing as follows:

Σ(Ei*Ti)/Σ(Ei)

where Ti is the determined timing information from a plurality of light sensors 34 (where i is an integer value greater than 0) and Ei is the determined energy information from the plurality of light sensors 34 (where i is the integer value).

As another example, the calculation the timing recovery information may be calculated as an energy weighted timing as follows:

Σ(Ti*sqrt(Ei))/Σ(sqrt(Ei))

where Ti is the determined timing information from a plurality of light sensors 34 (where i is an integer value greater than 0) and Ei is the determined energy information from the plurality of light sensors 34 (where i is the integer value).

Figure 7:
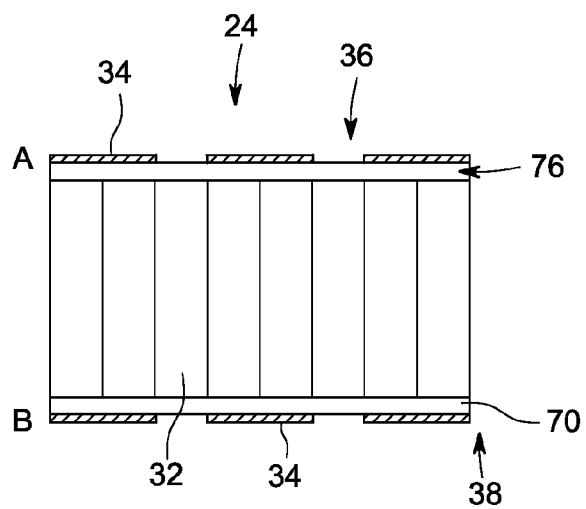
FIG. 7 is a diagram illustrating crystals of the detector unit of FIG. 5 showing lights sensors in accordance with another embodiment.

It should be noted that different weightings or timing calculations may be used in the various embodiments. Additionally, variations and modifications to the detector arrangements described herein may be provided. For example, as illustrated in FIG. 7, pairs of light sensors 34 may not be provided in connection with each of the crystals 32. For example, as illustrated in FIG. 7, two crystals 32 each include a pair of light sensors 34 with a crystal 32 between each of two other crystals 32 having pair of light sensors 34, not having any light sensors 34. Thus, two crystals 32 having light sensors 34 have adjacent crystals 32 on each end that do not have the light sensors 34. However, other variations are possible, such as three or more crystals 32 having light sensors 34 with adjacent crystals 32 on each end not having light sensors 32 or every other crystal 32 may have a pair of light sensors 34. It should be noted that in some embodiments, one or more crystals 32 may be partially covered by one or more light sensors 34. It also should be noted that any other combination may be used.

In the embodiment of FIG. 7, a light guide 70 is provided on each end of the crystals 32 between the ends 36 and 38 of the crystals 32 and the light sensors 34. The light guide may be formed from any light transport material that is used to transport light from the crystals 32 to the light sensors 34, such as from the crystals 32 that do not include the light sensor 34 to one of the other light sensors 34.

Figure 8:
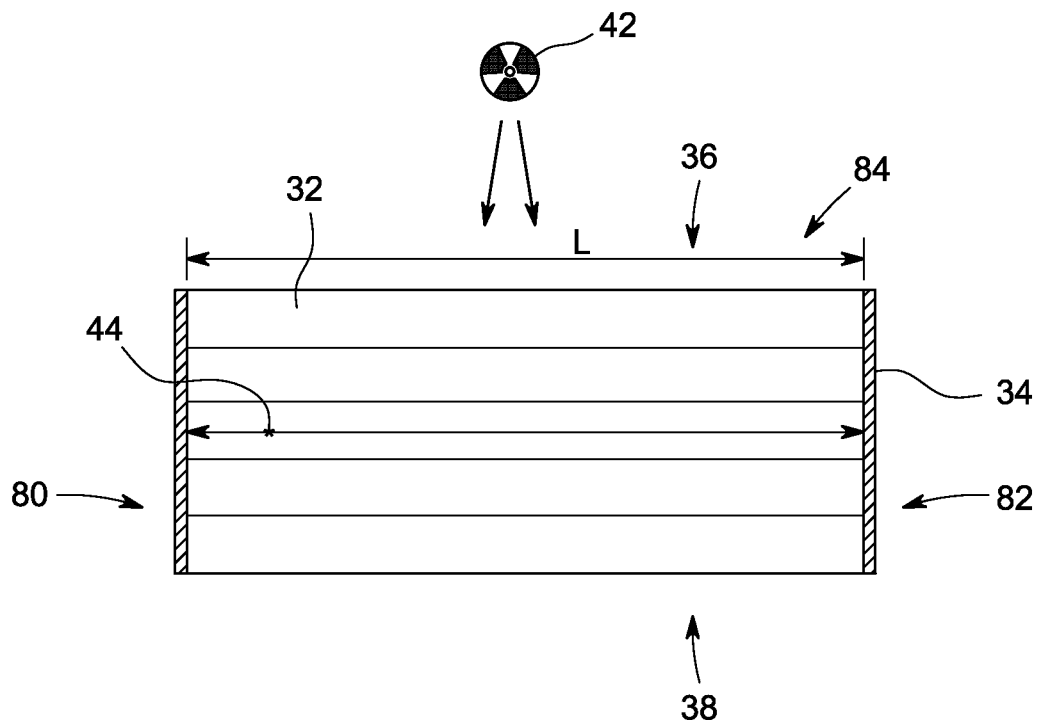
FIG. 8 is a diagram illustrating crystals of another detector unit having an axial placement of crystals and showing light sensors in accordance with an embodiment.

Other variations are contemplated. For example, as shown in FIG. 8, the light sensors 34 may be provided along sides 80 and 82 of the crystals 32 to form a detector 84. In this embodiment, the crystals 32 may be longer than the crystals 32 for the embodiments described above, such as having a length (L) of about 5 centimeters (cm) in some embodiments. In particular, the embodiment shown in FIGS. 8 and 9 includes an axial placement of the crystals 32 instead or a radial placements of the crystals 32, for example, as provided in FIG. 5. As described herein, the calculation of DOI is different, in addition to the difference in crystal length in some embodiments, as well as the cost of production.

Figure 9:
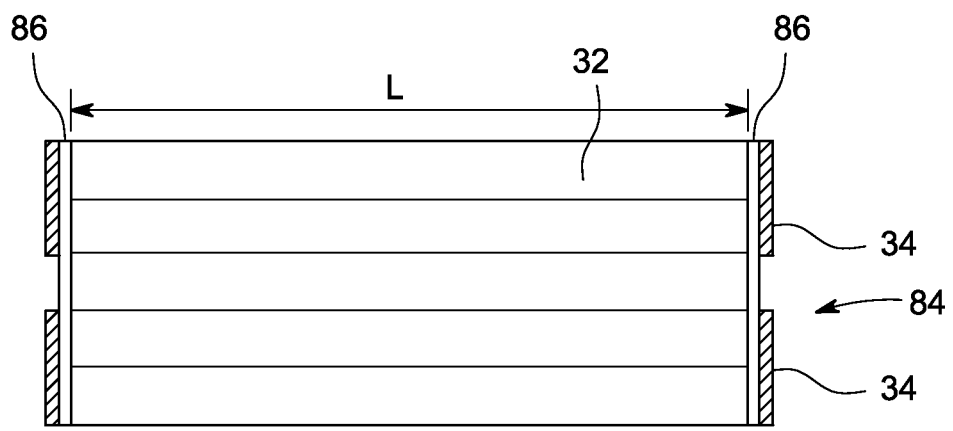
FIG. 9 is a diagram illustrating crystals of the detector unit of FIG. 8 showing lights sensors in accordance with another embodiment.

In this configuration, the interaction point 44 within a particular crystal 32 results in the visible light (which is isotropic visible light) traveling to the light sensors 34 on the sides 80 and 82, which then may be used to determine E1 and E2. The DOI information is determined based on which of the crystals 32 detected the gamma photon interaction, namely, which of the light sensors 34 detected visible light from the interaction event. This axial configuration in various embodiments may be a more cost-effective configuration than the radial configuration described herein. Similar to the embodiment of FIG. 7, light sensors 34 may not be provided in connection with each crystal 32 as illustrated in FIG. 9. In this embodiment, a light guide 86 is similarly provided.

Thus, using various embodiments, both the interaction point within the detector and timing correction information may be determined. This information may be used in any suitable method to reconstruct images, for example, based on one or more of the equations corresponding to the curves shown in FIG. 6. Additionally, it should be noted that different multiplexing schemes may be used to communicate the information from the various detectors described herein, such as to the PET detector electronics assembly 50 (shown in FIG. 1). For example, one such method is described in U.S. Patent Application Publication 2011/0210255, which is commonly owned.

Figure 10:
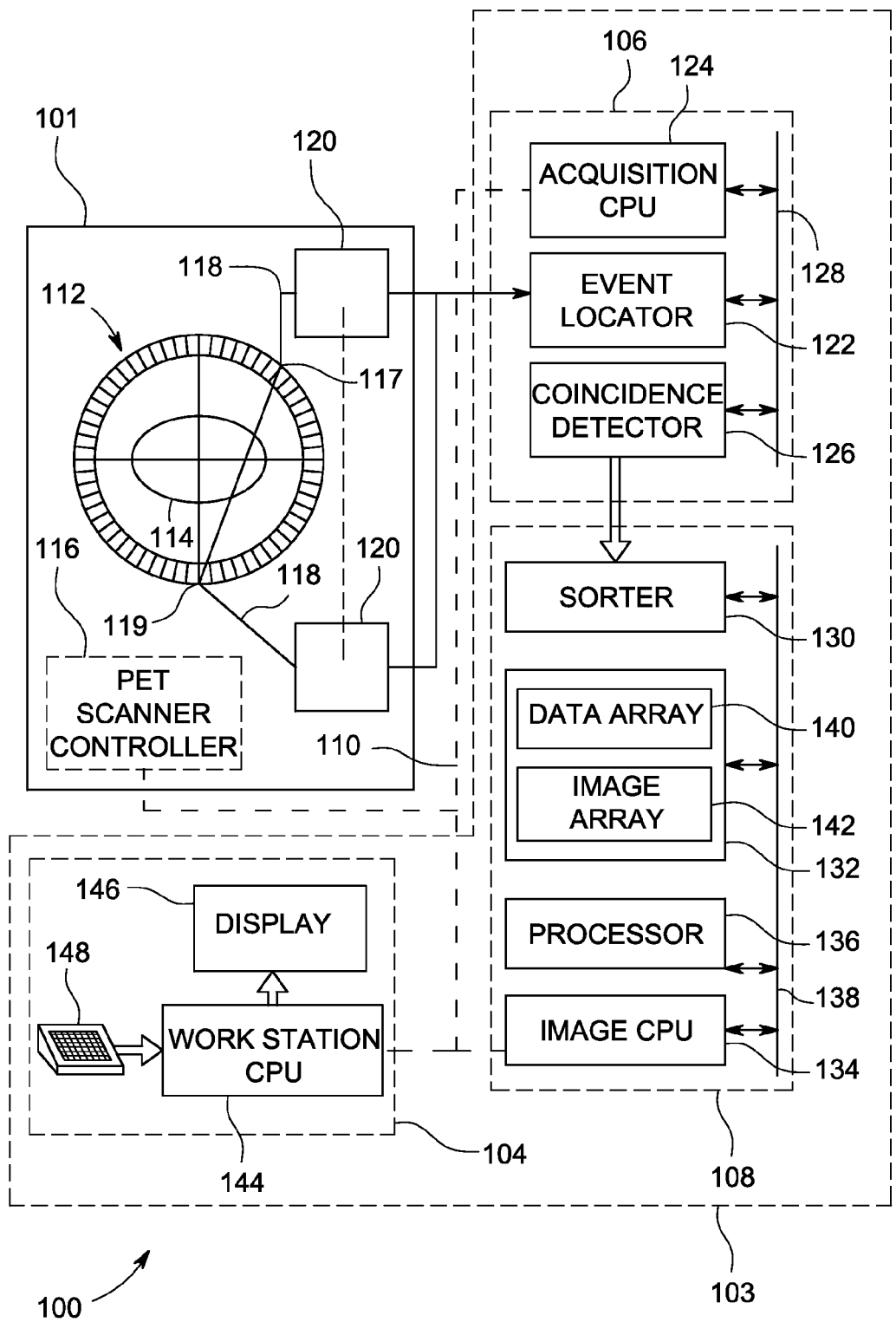
FIG. 10 is a diagram of a PET system in accordance with an embodiment.

FIG. 10 is a block diagram of an exemplary embodiment of a PET system 100 in which various embodiments of the invention may be implemented. The PET system 100 includes a PET scanner 101 and a controller 103 to control image reconstruction processes. The controller 103 is also configured to recover timing information based as described in more detail herein and may be embodied as the PET detector electronics assembly 50 (shown in FIG. 1). The controller 103 includes an operator workstation 104 and a processor 105. The processor 105 includes a data acquisition processor 106 and an image reconstruction processor 108. The PET scanner 101, operator workstation 104, data acquisition processor 106 and image reconstruction processor 108 are interconnected via a communication link 110 (e.g., a serial communication or wireless link). The PET scanner 101, which typically includes a gantry (not shown), acquires scan data and transmits the data to the data acquisition processor 106. The operation of the PET scanner 101 is controlled from operator workstation 104. The data acquired by data acquisition processor 106 is reconstructed using image reconstruction processor 108.

The PET scanner 101 may operate, using, for example, a plurality of detector rings. One such detector ring, detector ring 112, is illustrated in FIG. 10, which may be embodied as the detector ring assembly 20 (shown in FIG. 1). The detector ring 112 includes a central opening, in which an object 114 (e.g., a patient) may be positioned, using, for example, a motorized table that is aligned with the central axis of the ring 112. The motorized table moves the object 114 into the central opening of detector the ring 112, in response to one or more commands received from operator workstation 104. A PET scanner controller 116, also referred to as a gantry controller, is provided (e.g., mounted) in the PET scanner 101. The PET scanner controller 116 responds to the commands received from the operator workstation 104 through the communication link 110. Therefore, the operation of the PET scanner 101 is controlled from the operator workstation 104 through the PET scanner controller 116.

The detector ring 112 includes a plurality of detector elements for performing a PET scan of the object 114. For example, there may be 420 crystals per ring and 24 rings in the scanner. As shown in FIG. 10, the detector ring 112 includes a first detector element 117, a second detector element 119, and several other detectors. It should be noted that the detector elements are referred to as the first detector element and the second detector element, only to differentiate location in FIG. 1. The first detector element 117, like the other detectors, includes a set of scintillator crystals arranged in a matrix that is disposed in front of a plurality of photoensors (e.g., the light sensors 34) as described in more detail herein. When a photon collides with a crystal on a detector, the photon produces a scintilla on the crystal. Each photosensor produces an analog signal on the communication line 118 when a scintillation event occurs. A set of acquisition circuits 120 is provided within the PET scanner 101 to receive these analog signals. The acquisition circuits 120 produce digital signals indicating the location and total energy of the event. The acquisition circuits 120 also produce an event detection pulse that indicates the time at which the scintillation event was detected. These digital signals are transmitted through a communication link, for example, a cable, to an event locator circuit 122 in the data acquisition processor 106.

The data acquisition processor 106 includes the event locator 122, an acquisition CPU 124, and a coincidence detector 126. The data acquisition processor 106 periodically samples the signals produced by the acquisition circuits 120. The acquisition CPU 124 controls communications on a back-plane bus 128 and on the communication link 110. The event locator circuit 122 processes the information pertaining to each valid event and provides a set of digital numbers or values indicative of the detected event. For example, this information indicates when the event took place and the identity of the scintillation crystal that detected the event. An event data packet is communicated to the coincidence detector 126 through the back-plane bus 128. The coincidence detector 126 receives the event data packets from the event locator circuit 122 and determines if any two of the detected events are in coincidence. In this context, the coincidence is determined by a number of factors. First, the time markers in each event data packet must be within a predetermined time period, for example, 6 ns, of each other. Secondly, the LOR formed by a straight line joining the two detectors that detect the coincidence event should pass through the field of view in PET scanner 101. Events that cannot be paired are discarded. Coincident event pairs are recorded as a coincidence data packet that is communicated through a communication link to a sorter 130 in the image reconstruction processor 108.

The image reconstruction processor 108 includes the sorter 130, a memory module 132, an image CPU 134, an array processor 136, and a back-plane bus 138. The sorter 130 counts all events that occur along each projection ray and organizes them into a coincidence data set. In one embodiment, this data set is organized as a data array 140, referred to as a sinogram. The data array 140 is stored in the memory module 132. The back-plane bus 138 is linked to the communication link 110 through the image CPU 134, which controls communication through the back-plane bus 138. The array processor 136 is also connected to the back-plane bus 138, receives the data array 140 as an input, and reconstructs images in the form of the image arrays 142. The resulting image arrays 142 are stored in the memory module 132.

The images stored in the image array 142 are communicated by the image CPU 134 to the operator workstation 104. The operator workstation 104 includes a CPU 144, a display device 146, and an input device 148. The CPU 144 connects to the communication link 110 and receives inputs (e.g., user commands) from the input device 148, which may be, for example, a keyboard, mouse, or a touch-screen panel. The operator can control the calibration of the PET scanner 101, the configuration of the PET scanner 101, and the positioning of the object 114 for a scan through the input device 148 and associated control panel switches. Similarly, the operator can also control the display of the resulting image on the display device 146 and perform image-enhancement functions, using programs executed by the workstation CPU 144.

The processor 105 is configured to process the scan data received from the detector elements. The scan data includes, for example, sinogram and timing information that is received by processor 105 from the detector elements during an imaging scan. The timing information in one embodiment is the difference in time at which two photons emitted in an annihilation event are detected by detector elements. The timing information may include time stamp information relating to a measured photon event detected by a pair of detector elements, for example, the first detector element 117 and the second detector element 119, for the PET system 100. The time stamp information is the time at which each photon is detected by a detector element, which in various embodiments include two times for each detector, namely the time the interaction was detected by each of the pair of light sensors 34 (shown in FIGS. 2-5 and 7-9). Further, the processor 105 is configured to process the energy and timing data, as described in more detail herein. The energy and timing information may be used to perform timing recovery as described herein.

The timing information is received by detectors, which include, for example, a block of 36 scintillator crystals attached to an array of photosensors. The scintillator crystals convert the incoming photon from the patient into a plurality (e.g., several thousand) of light photons (e.g., visible or near UV), which are detected by the photosensors. The proportion of light photons detected by each photosensor channel is used to determine which of the 36 crystals received the incoming photon. The timing signal is determined by processing the leading edge of the signals, to estimate the arrival of the light photons at the light sensors 34 of, for example, the SiPM. This timing signal is then digitized and processed subsequently.

The timing information may be received from the TOF PET system during an image acquisition scan of an object using any suitable method. Based on the received information, an image of the object is reconstructed.

The energy and timing information are used to reconstruct an image of the object 114, scanned by the PET system 100. The reconstruction may include, for example, a two-dimensional or three-dimensional reconstruction. The timing data of each detector element may be configured as a timing bias matrix with a timing recovery value for each set of projection rays of the PET system 100. It should be noted that a detector element pair detects the projection rays from a photon event. The timing bias data of each detector element pair corresponding to the projection ray is stored in the memory module 132 of the PET system 100.

In the reconstruction of an image, the timing recovery information may be used to determine the point along a line joining a pair of detector elements at which a gamma photon event occurred. For example, from the energy and timing recovery information, and using a conversion factor of 15 cm/ns, which is half the speed of light (half the speed of light is used because two photons are traveling in opposite directions simultaneously), the timing recovery information may be used to determine a distance between the detectors at which the photon event occurred. Therefore, if there is a photon event with a timing difference of zero, this generally indicates that the photon event occurred at the midpoint of the line joining the two detector elements.

Different types of image reconstruction algorithms may be used to reconstruct an image in the TOF PET system, for example, an analytical image reconstruction (e.g., confidence-weighted filtered-back projection) and an iterative reconstruction (e.g., confidence-weighted maximum-likelihood expectation maximization). Both of these algorithms for image reconstruction are based on the fundamental operation of confidence-weighted back-projection, which converts the counts detected by a detector element pair/time bin combination back into image space. This is performed by distributing the counts (in appropriate proportions) to appropriate locations along the line joining the two detector elements, based on the probability that a coincidence event arising from that location will produce the measured timing difference. It should be noted that any reconstruction algorithm may be used or modified as desired or required. It should also be noted that in one embodiment, the TOF PET system includes multiple timing bins, each corresponding to a different measured timing difference. Each time bin represents a different location on the line joining two detector elements, for example, the first detector element 117 and the second detector element 119. The bin representing time t=0 represents the midpoint between the two detector elements. The bins with positive time stamps are located towards one detector element, while those with negative time stamps are located towards the other detector element.

If there are timing recovery values for the detector elements, for example, as determined by the timing recovery methods described herein, the assignment process as described above, is shifted in proportion to the this information corresponding to each detector element pair.

Figure 11:
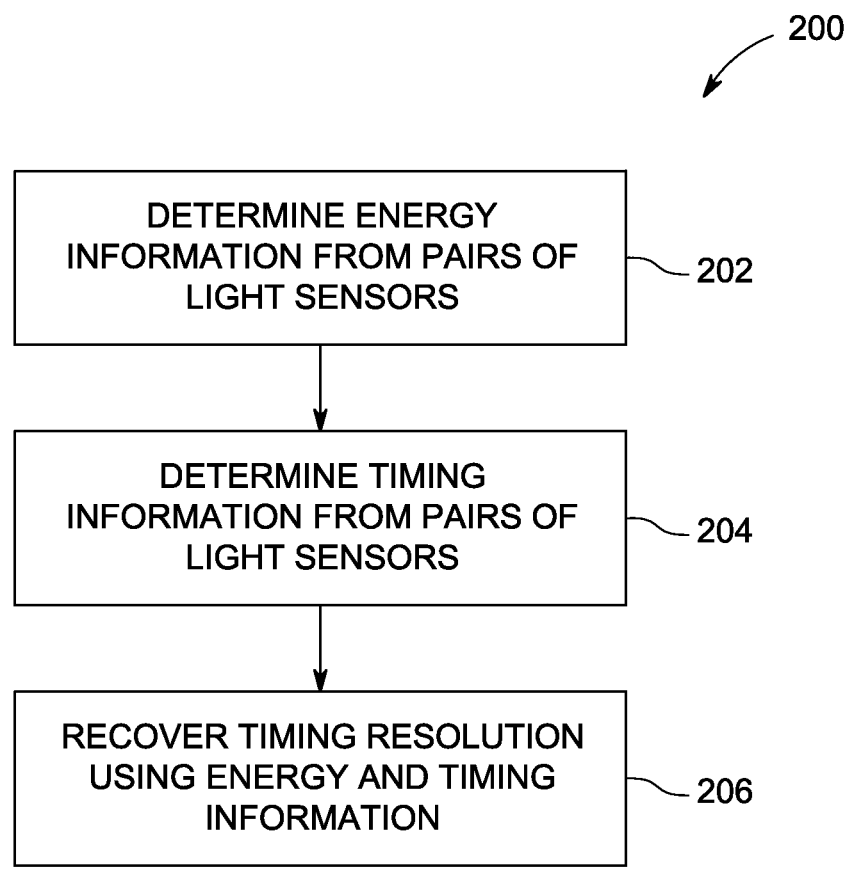
FIG. 11 is a flowchart of a method for recovering timing information in a PET detector in accordance with various embodiments.

Various embodiments also provide a method 200 as shown in FIG. 11 for recovering timing information in a TOF PET detector. The method 200 includes determining energy information from pairs of light sensors at 202. For example, as described in more detail herein, light sensors at ends or side of scintillator crystals are used to determine the energy of a gamma photon interaction within the crystal. Additionally, timing information is determined from the pairs of light sensors at 204. For example, as described in more detail herein, the light sensors identify the time at which the isotropic light within the crystal reaches each of the light sensors, thereby defining timing correction information. Using the energy and timing information, timing resolution recovery may be performed at 206. For example, as described herein timing recovery information may be determined using an energy weighted timing equation or a sqrt(E) weighted timing equation. This timing recovery information is then used in any suitable image reconstruction technique, such as to provide an offset or additional timing bias.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A method for determining timing recovery information in a Time-of-Flight (TOF) Positron Emission Tomography (PET) system, said method comprising:
   determining energy information from pairs of light sensors of detectors of the TOF PET system, wherein the pairs of light sensors are at opposite sides of scintillator crystals of the detectors;
   determining timing information from the pairs of light sensors of the detectors of the TOF PET system; and
   calculating timing recovery information using the determined energy and timing information, wherein the energy information, the timing information, and the timing recovery information are devoid of simulation data.

2. The method of claim 1, wherein calculating the timing recovery information comprises using a ratio of the determined energy information.

3. The method of claim 1, wherein calculating the timing recovery information comprises calculating a weighted timing using the determined timing information.

4. The method of claim 1, wherein calculating the timing recovery information comprises calculating an energy weighted timing using:

$$\Sigma(T_i * E_i)/\Sigma(E_i)$$

where Ti is the determined timing information from a plurality of light sensors and Ei is the determined energy information from the plurality of light sensors.

5. The method of claim 1, wherein calculating the timing recovery information comprises calculating a square-root energy sqrt(E) weighted timing using:

$$\Sigma(T_i * \mathrm{sqrt}(E_i))/(\mathrm{sqrt}(E_i))$$

where Ti is the determined timing information from a plurality of light sensors and Ei is the determined energy information from the plurality of light sensors.

6. The method of claim 1, wherein calculating the timing recovery information comprises calculating full width at half maximum (FWHM) timing information using 1/T-FWHM.

7. The method of claim 1, further comprising determining a depth of interaction based on a scintillator crystal that detected a photon interaction event.

8. The method of claim 1, further comprising determining depth of interaction information (DOI) for a crystal of the detector from the timing information from the pairs of light sensors of the detectors.

9. The method of claim 8, further comprising correcting a time stamp by an amount of a transit time calculated from a DOI point in the crystal.

10. A Time-of-Flight (TOF) Positron Emission Tomography (PET) system comprising:
 a plurality of detector elements configured to acquire scan data, the detector elements having scintillator crystals with pairs of light sensors, wherein the pairs of light sensors are at opposite sides of scintillator crystals, wherein the scan data is devoid of simulation data; and
 a processor configured to calculate timing recovery information by determining energy information from the pairs of light sensors of detectors and determining timing information from the pairs of light sensors.

11. The TOF PET system of claim 10, wherein the processor is configured to calculate the timing recovery information using a ratio of the determined energy information.

12. The TOF PET system of claim 10, wherein the processor is configured to calculate the timing recovery information by calculating a weighted timing using the determined timing information.

13. The TOF PET system of claim 10, wherein the processor is configured to calculate the timing recovery information by calculating an energy weighted timing using:

$$\Sigma(Ei*Ti)/\Sigma(Ei)$$

where Ti is the determined timing information from a plurality of light sensors and Ei is the determined energy information from a plurality of light sensors.

14. The TOF PET system of claim 10, wherein the processor is configured to calculate the timing recovery information by calculating a square-root energy sqrt(E) weighted timing using:

$$\Sigma(Ti*sqrt(Ei))/\Sigma(sqrt(Ei))$$

where Ti is the determined timing information from a plurality of light sensors and Ei is the determined energy information from the plurality of light sensors.

15. The TOF PET system of claim 10, wherein the processor is configured to calculate the timing recovery information by calculating full width at half maximum (FWHM) timing information using 1/T-FWHM.

16. The TOF PET system of claim 10, wherein the processor is configured to determine a depth of interaction based on the scintillator crystal that detected a photon interaction event.

17. A non-transitory computer readable storage medium to determine timing recovery information for a Time-of-Flight (TOF) Positron Emission Tomography (PET) system using a processor, the non-transitory computer readable storage medium including instructions to command the processor to:
 determine energy information from pairs of light sensors of detectors of a TOF PET system, wherein the pairs of light sensors are at opposite sides of scintillator crystals of the detectors;
 determine timing information from the pairs of light sensors of the detectors of the TOF PET system; and
 calculate timing recovery information using the determined energy and timing information, wherein the energy information, the timing information, and the timing recovery information are devoid of simulation data.

18. The non-transitory computer readable storage medium of claim 17 including instructions to further command the processor to calculate the timing recovery information using a ratio of the determined energy information and calculate the timing recovery information by calculating a weighted timing using the determined timing information.

19. The non-transitory computer readable storage medium of claim 17, wherein the instructions to command the processor to calculate timing recovery information using the determined energy and timing information includes instructions to command the processor to calculate the timing information by calculating one or more of (a) an energy weighted timing using: $\Sigma(Ti*Ei)/\Sigma(Ei)$, where Ti is the determined timing information from a plurality of light sensors and Ei is the determined energy information from the plurality of light sensors, (b) a square-root energy sqrt(E) weighted timing using: $\Sigma(Ti*sqrt(Ei))/(sqrt(Ei))$, where Ti is the determined timing information from a plurality of light sensors and Ei is the determined energy information from the plurality of light sensors, or (c) full width at half maximum (FWHM) timing information using 1/T-FWHM.

20. A method for determining timing recovery information in a Time-of-Flight (TOF) Positron Emission Tomography (PET) system, said method comprising:
 determining energy information from pairs of light sensors of detectors of the TOF PET system;
 determining timing information from the pairs of light sensors of the detectors of the TOF PET system; and
 calculating timing recovery information using the determined energy and timing information, wherein the calculating timing recovery information comprises calculating one or more of (a) an energy weighted timing using: $\Sigma(Ti*Ei)/\Sigma(Ei)$, where Ti is the determined timing information from a plurality of light sensors and Ei is the determined energy information from the plurality of light sensors, (b) a square-root energy sqrt(E) weighted timing using: $\Sigma(Ti*sqrt(ED)/(sqrt(Ei))$, where Ti is the determined timing information from a plurality of light sensors and Ei is the determined energy information from the plurality of light sensors, or (c) full width at half maximum (FWHM) timing information using 1/T-FWHM.

21. A Time-of-Flight (TOF) Positron Emission Tomography (PET) system comprising:
 a plurality of detector elements configured to acquire scan data, the detector elements having scintillator crystals with pairs of light sensors; and
 a processor configured to calculate timing recovery information by determining energy information from the pairs of light sensors of detectors and determining timing information from the pairs of light sensors,
 wherein the processor is configured to calculate the timing recovery information by calculating one or more of (a) an energy weighted timing using: $\Sigma(Ti*Ei)/\Sigma(Ei)$, where Ti is the determined timing information from a plurality of light sensors and Ei is the determined energy information from the plurality of light sensors, (b) a square-root energy sqrt(E) weighted timing using: $\Sigma(Ti*sqrt(Ei))/(sqrt(Ei))$, where Ti is the determined timing information from a plurality of light sensors and Ei is the determined energy information from the plurality of light sensors, or (c) full width at half maximum (FWHM) timing information using 1/T-FWHM.

22. A non-transitory computer readable storage medium to determine timing recovery information for a Time-of-Flight (TOF) Positron Emission Tomography (PET) system using a processor, the non-transitory computer readable storage medium including instructions to command the processor to:
 determine energy information from pairs of light sensors of detectors of a TOF PET system;
 determine timing information from the pairs of light sensors of the detectors of the TOF PET system; and
 calculate timing recovery information using the determined energy and timing information, wherein the instructions to command the processor to calculate timing recovery information using the determined energy and timing information include instructions to command the processor to calculate the timing information by calculating one or more of (a) an energy weighted timing using: $\Sigma(T_i*E_i)/\Sigma(E_i)$, where $T_i$ is the determined timing information from a plurality of light sensors and $E_i$ is the determined energy information from the plurality of light sensors, (b) a square-root energy sqrt(E) weighted timing using: $\Sigma(T_i*sqrt(E_i))/(sqrt(E_i))$, where $T_i$ is the determined timing information from a plurality of light sensors and $E_i$ is the determined energy information from the plurality of light sensors, or (c) full width at half maximum (FWHM) timing information using 1/T-FWHM.

* * * * *